United States Patent
Nelson (10) Patent No.: US 6,180,598 B1
(45) Date of Patent: Jan. 30, 2001

(54) COVALENTLY MODIFIED HEMOGLOBIN HAVING LOW TEMPERATURE-DEPENDENT OXYGEN-BINDING FUNCTION

(76) Inventor: Deanna J. Nelson, 104 Tasman Ct., Cary, NC (US) 27513-2922

( * ) Notice: Under 35 U.S.C. 154(b), the term of this patent shall be extended for 0 days.

(21) Appl. No.: 09/413,933

(22) Filed: Oct. 7, 1999

(51) Int. Cl.$^7$ .......................... A61K 38/42; C07K 14/805
(52) U.S. Cl. ................................................ 514/6; 530/385
(58) Field of Search .................................. 530/385; 514/6

(56) References Cited

U.S. PATENT DOCUMENTS

| | | | |
|---|---|---|---|
| Re. 34,271 | 6/1993 | Walder | 530/385 |
| 4,301,144 | 11/1981 | Iwashita | 530/385 |
| 4,600,531 | 7/1986 | Walder | 530/408 |
| 5,128,452 | 7/1992 | Hai | 530/385 |
| 5,585,484 | * 12/1996 | Acharya et al. | 540/145 |
| 5,599,907 | * 2/1997 | Anderson et al. | 530/385 |
| 5,900,402 | 5/1999 | Shorr | 530/385 |

OTHER PUBLICATIONS

Hai et al. Polymerization of Diaspirin Crosslinked Hemoglobin . . . Tetrahedron. vol. 55, pp. 2147–2156, 1999.*
Rogers et al. Effects of polymerization on the oxygen . . . Biochim. Biophys. Acta. vol. 1248, pp. 135–142, 1995.*
Willford, David C. and Hill, Esther P. "Modest effect of temperature . . . " Respiration Physiology 1986; 64:113–123.
Zijlstra, Willem G, Anton HJ Maas, Robert F. Moran. "Definition, significance and measurement of quantities of human blood." Scand J Clin Lab Invest 1996; 56, Suppl 224: 24–45.

* cited by examiner

*Primary Examiner*—Jeffrey E. Russel
(74) *Attorney, Agent, or Firm*—Deanna J. Nelson (57) ABSTRACT

The present invention provides various covalently modified hemoglobin compositions, each having a low temperature-dependent oxygen-binding function. The present invention also provides methods for preparing the hemoglobin compositions wherein a hemoglobin is intra-molecularly cross-linked and covalently modified with a class of hydrodynamic volume-enhancing, anionic compounds. The present invention also provides therapeutic, oxygen-delivering compositions comprising the hemoglobin compositions and pharmaceutically useful vehicles. Moreover, the present invention provides methods for delivering oxygen to cells or tissues using these compositions.

22 Claims, 1 Drawing Sheet

COVALENTLY MODIFIED HEMOGLOBIN HAVING LOW TEMPERATURE-DEPENDENT OXYGEN-BINDING FUNCTION

CROSS-REFERENCE TO RELATED APPLICATIONS

None

STATEMENT REGARDING FEDERALLY SPONSORED RESEARCH & DEVELOPMENT

No Federally sponsored research & development was used in making this invention.

BACKGROUND OF THE INVENTION

The restoration of oxygen delivery is a key survival factor for humans and other mammals following oxygen deprivation, such as that which results from blood loss (global ischemia) or restrictions to blood flow following myocardial infarction or stroke (focal ischemia). Transfusion of warmed (37° C.) blood or packed red cells restores the circulating fluid volume and oxygen delivery following hemorrhage, but is not useful as a means for restoring oxygen delivery to tissues where the circulation has been impeded. Conversely, since hemoglobin (Hb) is much smaller in size than the red cell and is recognized as the natural oxygen transporting protein in mammals, solutions of this protein have the potential both to restore the circulating volume and to perfuse areas where the circulation has been compromised by infarcts. Thus, Hb solutions have been studied extensively as potential resuscitative fluids for the restoration of oxygen delivery.

However, native mammalian Hbs have two significant shortcomings that negate their therapeutic utility for the restoration of oxygen delivery following oxygen deprivation. First, following their isolation from red cells and purification, the oxygen affinity of native mammalian Hbs is too high to allow for effective oxygen delivery to ischemic tissues in vivo. Second, native mammalian Hbs break down in the circulatory system into alpha chain- or beta chain-containing subunits having dose-related nephrotoxicity.

These two shortcomings have been addressed by covalent modification of Hb. As a result of modification, Hb compositions have been produced that cannot break down into subunits and also have therapeutically useful oxygen binding properties at pH 7.4 and 37° C. Four general types of Hb modification are recognized: (1) intra-molecular cross-linking; (2) modification of amino acid residues on the surface of the protein ("decoration"); (3) polymerization; and (4) combinations of intra-molecular cross-linking with decoration and/or polymerization.

Hypothermia is a corollary treatment that is used in surgeries of the heart and brain, two organs that are very sensitive to oxygen deprivation, and in organ, tissue or cell preservation. Under hypothermic conditions the patient's body temperature (or the temperature of the organ, tissue or cell) is lowered from about 37° C. to about 20° C. As the temperature is decreased, both blood and many mammalian Hbs, both native and covalently modified, show an increase in oxygen affinity that adversely affects their oxygen delivery capability. As a consequence of this increase in oxygen affinity of the Hb, neither blood or any of the known Hb compositions has the capability to maintain therapeutically effective oxygen delivery at these low temperatures. Oxygen deprivation (ischemia) results.

Accordingly, there exists a therapeutic need for new covalently modified hemoglobin compositions having an oxygen affinity that is less adversely affected by decreases in temperature, i.e., hemoglobin compositions having a low temperature-dependent oxygen binding function. The present invention satisfies this need.

BRIEF SUMMARY OF THE INVENTION

The present invention provides a covalently modified hemoglobin composition having an oxygen binding function that exhibits low temperature-dependence.

Moreover, the present invention provides a covalently modified hemoglobin composition wherein the subunits of the hemoglobin have been joined covalently by reaction of amino groups on the subunits of the protein with a heteropolyfunctional, intra-molecular cross-linker having the formula:

wherein X is selected from the group consisting of halide, sulfonate, phosphate, phosphonate, azide, oxirane, thiirane, azirane, maleimide and formyl; n is an integer from 0 to 8; and Y is a substituted activating ester or substituted activating thioester, wherein the activating esters are substituted with at least one anionic group selected from the group consisting of carboxyl, sulfate, sulfite, phosphonate, and phosphate; and each of at least five of the thiyl or amino groups on the surface of Hb has been joined covalently to a hydrodynamic volume-enhancing, anionic ligand having the formula:

wherein m is an integer from 1 to 100; and Z is $CH_2$—Hb, $CH(OH)CH_2$—Hb, $CH(SH)CH_2$—Hb, Moreover, the invention provides a method for delivering oxygen to cells or tissues comprising exposing said cells or tissues to a covalently modified hemoglobin composition of the present invention.

BRIEF DESCRIPTION OF THE FIGURES

$$P_{50,T} = 10^{\left[\log P_{50,37} - \left[\frac{d(\log P_{50})}{dT} \times (37-T)\right]\right]}$$

where $P_{50,T}$ is the $P_{50}$ value (mmHg) of the Hb at temperature T(°C.); $P_{50,37}$ is the $P_{50}$ value (mmHg) of the Hb at 37° C. and pH 7.4; and d(log $P_{50}$)/dT is the temperature dependence of the $P_{50}$ value of the Hb. The calculated data points are presented in Table 1. The data in Columns C-G of the Table were calculated assuming the Hb had a $P_{50}$ value of about 27 mmHg at 37° C. and a pH of 7.4. The data in Column B illustrate the shortcoming of human Hb (in fresh human blood) having a $P_{50}$ value of about 27 mmHg at 37° C. and a pH of 7.4 and a d(log $P_{50}$)/dT of 0.023 units per degree Celsius, for which the $P_{50}$ value decreases to 11 mmHg at 20° C.; this latter value indicates an oxygen affinity of human Hb at 20° C. too high to permit effective oxygen delivery by human Hb. Conversely, the data in Column A illustrate the advantage of a covalently modified porcine hemoglobin composition of the instant invention having a $P_{50}$ value of about 35 mmHg at 37° C. and a pH of 7.4 and a d(log $P_{50}$)/dT value of 0.016 units per degree Celsius; at 20° C. and a pH of 7.4 the $P_{50}$ value of this Hb is 19.2 mmHg, a value indicating an oxygen affinity sufficiently low to permit effective oxygen delivery by this Hb. The data in columns C-G disclose the manner in which a decrease in the temperature dependence of the oxygen binding function of a covalently modified Hb of the instant invention favorably increases the $P_{50}$ value of the Hb at temperatures lower than 37° C., i.e., favorably decreases the oxygen affinity of the Hb.

Figure 1:
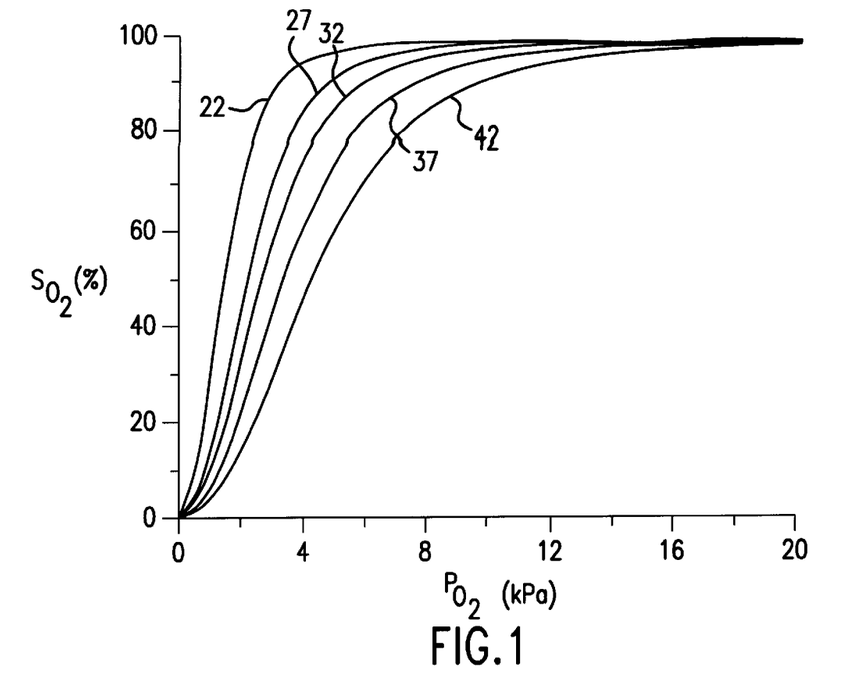
FIG. 1 is a graph of the oxygen binding function of the hemoglobin in human blood having a pH 7.4 and a partial pressure of $CO_2$ of 5.3 kPa. The oxygen binding function is the curve disclosing the relationship between the percent oxygen saturation of a Hb [$S_{O2}$ (%)] and the partial pressure of oxygen under the specified conditions [$P_{O2}$ (kPa)]. For each determination, the temperature (in degrees Celcius) of the water bathing the measurement cell containing the blood was adjusted to the value shown above the respective curve. The blood was deoxygenated and then allowed to equilibrate with atmospheres containing increasing partial pressures of oxygen. The percent Hb saturation vs. partial pressure of oxygen data are displayed graphically to define the oxygen binding function at that temperature and to enable calculation of the $P_{50}$ value of the hemoglobin at that temperature. By convention, the $P_{50}$ of a Hb is the partial pressure of oxygen (in mmHg) at which the Hb is 50% oxygen-saturated.
Figure 2:
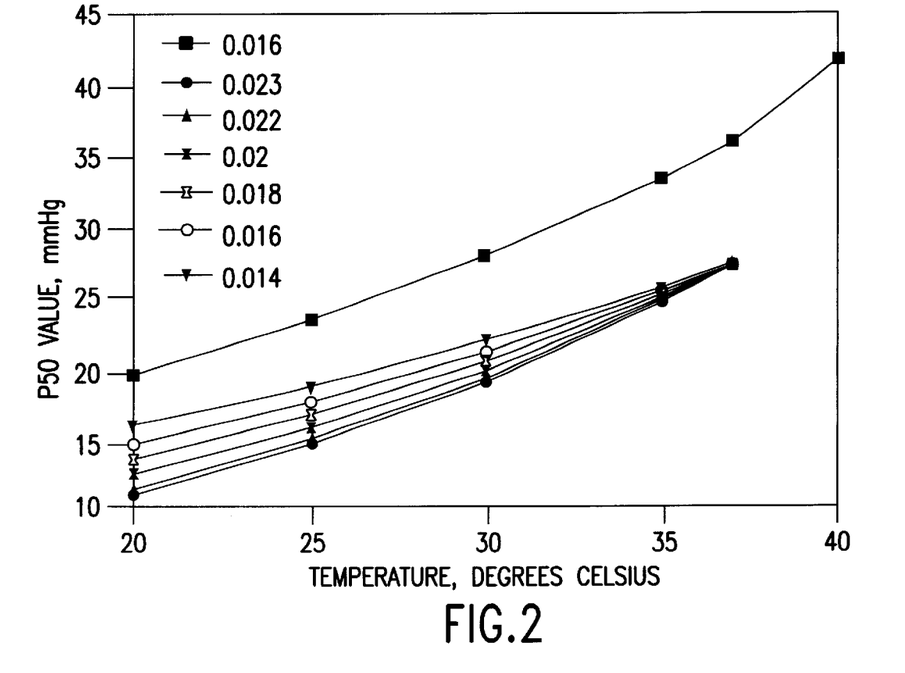
FIG. 2 is a graph illustrating the effect of decreases in temperature [i.e., the temperature dependence or d (log $P_{50}$)/dT] on the $P_{50}$ of native human Hb [for which d (log $P_{50}$)/dT=0.023 units per degree Celsius] and hemoglobins having an oxygen binding function having a temperature dependence of 0.022, 0.020, 0.018, 0.016 or 0.014 units per degree Celsius. Data points for each line were calculated using the equation.

tion exhibits a temperature dependence (d log $P_{50}$/dT) of less than 0.023 units per degree Celsius.

In accordance with the present invention, the term "biocompatible pH" means a pH of 6.5–8.5 at 37° C. Although we are not bound by any particular interpretation or theory, it is believed that mammalian cells or tissues tolerate values of pH in this range. In particular, it is believed that human cells or tissues tolerate values of pH in this range.

The oxygen binding function of a Hb is a characteristic property of each Hb when measured under standardized conditions. However, when a Hb is chemically modified, for example, by the attachment of substituents or by the substitution of amino acids, the oxygen binding function changes in an unpredictable manner. Thus, the oxygen binding function of a covalently modified Hb differs from that of the native Hb from which it is derived and cannot be predicted a priori. This function must be determined experimentally.

In accordance with conventional practice, the oxygen binding function of a hemoglobin is determined by monitoring the change in the percentage of hemoglobin saturation as the partial pressure of oxygen in the atmosphere is changed (W. G. Zijlstra et al. Definition, significance and measurement of quantities pertaining to the oxygen carrying properties of human blood. Scand. J. Clin. Lab. Invest. 56, Suppl. 224: 27–45, 1996). By convention, the $P_{50}$ value of a Hb is the partial pressure of oxygen in mmHg when the Hb is 50% oxygen-saturated.

The oxygen binding function of a Hb varies with the temperature, i.e., the oxygen binding function exhibits temperature dependence (M. P. Hlastala, R. D. Woodson and B. Wranne, Influence of temperature on hemoglobin-ligand interaction in whole blood. J. Appl. Physiol. 43: 545–550, 1977). The temperature dependence of the oxygen binding function of a Hb is determined by measuring the oxygen binding function of a Hb at various temperatures using a Hemox-Analyzer instrument. For each determination, the temperature of the water bathing the measurement cell is adjusted to a value in the range from 0° C. to 40° C. A solution of the Hb in Hemox buffer is placed in the cell and deoxygenated by equilibration with nitrogen gas. When deoxygenation is complete, a measurement is taken. Then the Hb is allowed to equilibrate with atmospheres containing increasing partial pressures of oxygen. The percent satura-

TABLE 1

Change in $P_{50}$ Value (mmHg) of Hb With Temperature $P_{50}$ Value, mmHg

| Temperature, ° C. | (A) 0.016* | (B) 0.023* | (C) 0.022* | (D) 0.020* | (E) 0.018* | (F) 0.016* | (G) 0.014* |
|---|---|---|---|---|---|---|---|
| 40 | 41.6 | — | — | — | — | — | — |
| 37 | 35.7 | 27 | 27 | 27 | 27 | 27 | 27 |
| 35 | 33.2 | 24.3 | 24.4 | 24.6 | 24.9 | 25.1 | 25.3 |
| 30 | 27.8 | 18.6 | 18.9 | 19.6 | 20.2 | 20.9 | 21.6 |
| 25 | 23.1 | 14.3 | 14.7 | 15.5 | 16.4 | 17.4 | 18.3 |
| 20 | 19.2 | 11.0 | 11.4 | 12.3 | 13.4 | 14.4 | 15.6 |

*The value of d (log $P_{50}$)/dT used in this calculation.

DETAILED DESCRIPTION OF THE INVENTION

The present invention provides a covalently modified hemoglobin composition having a biocompatible pH and an oxygen binding function, wherein the oxygen binding function of the Hb is monitored spectrophotometrically, and the measurements are recorded. The percent Hb saturation vs. partial pressure of oxygen data are displayed graphically to define the oxygen binding function at that temperature and to enable calculation of the $P_{50}$ value of the hemoglobin at that temperature. In turn, the logarithms of the $P_{50}$ data are displayed graphically vs. the corresponding temperatures to determine the temperature dependence of the oxygen binding function (i.e., the slope of the resulting line). In accordance with the present invention, the temperature dependence of the oxygen binding function of a Hb [i.e., d (log $P_{50}$)/dT] is the change in the logarithm of the $P_{50}$ value of a Hb with respect to the change in temperature in degrees Celsius. In accordance with the present invention, the temperature dependence of the oxygen binding function is a value in "units per degree Celsius."

A covalently modified hemoglobin composition of the instant invention has a biocompatible pH and an oxygen binding function which has a temperature-dependence [i.e., d (log $P_{50}$)/dT] of less than 0.023 units per degree Celsius. In a preferred embodiment of the invention, the oxygen binding function of the covalently modified hemoglobin composition has a temperature dependence of equal to or less than 0.020 units per degree Celsius. In a most preferred embodiment of the invention, the oxygen binding function of the covalently modified hemoglobin composition has a temperature dependence of equal to or less than 0.016 units per degree Celsius.

The present invention also provides a covalently modified hemoglobin composition wherein (a) two of the subunits of a hemoglobin are covalently joined by an intra-molecular bridge (i.e., intra-molecularly cross-linked) to prevent dissociation of the subunits, and (b) each of at least five amino or thiyl groups on the surface of the Hb is modified covalently to increase the hydrodynamic volume of the Hb (i.e., the Hb is decorated). In a preferred embodiment, said covalently modified hemoglobin compositions comprise Hb having an intra-molecular bridge covalently joining the alpha, alpha or beta, beta subunits of a native mammalian or recombinant Hb and further having each of at least five thiyl or amino groups on the surface of the protein covalently joined to a hydrodynamic volume-enhancing, anionic ligand. Covalently modified hemoglobin compositions of the instant invention have an isoelectric point and net surface charge very similar to those of the native mammalian or recombinant Hb that was used in their preparation, a feature that enhances their stability and compatibility with cells or tissues.

A covalently modified hemoglobin composition of the present invention may be prepared by covalent modification of a purified mammalian or recombinant Hb. A mammalian Hb may be obtained in useful quantities by isolating the Hb from the red blood cells of a mammal and purifying it. In a preferred embodiment of the present invention, porcine Hb is isolated from pig erythrocytes and further purified prior to covalent modification in accordance with the present invention. If pathogen inactivation of the purified mammalian Hb solution is desired, it may be effected by pasteurization of unliganded or CO-liganded Hb using conventional techniques (T. Asakura et al. Molecular stability of Hb Philly ($\alpha_2\beta_2$ $^{35}$((C1)Tyr-Phe)). The relationship of hemoglobin stability to ligand state as defined by heat and mechanical shaking tests. Hemoglobin 5/2: 177–190, 1981).

Alternatively, to avoid potential concerns about virus or pathogen contamination of the mammalian hemoglobin (B. N. Manjula et al. Correct assembly of human normal adult hemoglobin when expressed in transgenic swine: chemical, conformational and functional equivalence with the human-derived protein. Protein Engin. 11: 583–588, 1998.), a recombinant Hb may be expressed, isolated and purified using conventional means. In another preferred embodiment of the present invention, a recombinant Hb is expressed, isolated and purified prior to covalent modification in accordance with the present invention.

In accordance with the present invention, a purified mammalian or recombinant Hb is intra-molecularly cross-linked by reacting with a compound having the formula:

wherein X is selected from the group consisting of halogen, sulfonate, phosphate, phosphonate, azide, oxirane, thiirane, azirane, maleimide and formyl; n is an integer from 0 to 8; and Y is a substituted activating ester or substituted activating thioester, wherein the activating esters are substituted with at least one anionic function selected from the group consisting of carboxyl, sulfate, sulfite, phosphonate, and phosphate. The use of activating esters or activating thioesters facilitates completion of the intra-molecular cross-linking reaction in a practical period of time (R. L. Lundblad. "Chemical Reagents for Protein Modification." CRC Press, Inc., Boca Raton, Fla., 1991). If the activating ester or thioester is substituted with at least one anionic function, electrostatic interaction with the Hb at anion-binding sites on the protein will be enhanced (M. F. Perutz. The Bohr effect and combination with organic phosphates. Nature 228: 734, 1970; H. Ueno et al. Random chemical modification of the oxygen-linked chloride-binding sites of hemoglobin: those in the central dyad axis may influence the transition between deoxy- and oxy-hemoglobin. J. Protein Chem. 12, No. 5: 561–570, 1993). This is desirable in that intra-molecular cross-linking at one or more specific sites on the protein is facilitated thereby.

It is preferred that the ratio of the moles of cross-linking compound to moles of Hb be about two, although molar ratios of from about one to about five are useful. The concentration of Hb is preferably about 3 g/dL to about 6 g/dL, although higher or lower Hb concentrations may be used. Prior to reaction with the compound, the Hb is converted to deoxyHb by degassing using conventional means. The reaction is performed at pH values of 6.5–8.5, and preferably at neutral pH. A reaction temperature of about 25° C. is preferred, but a reaction temperature in the range from about 4° C. to about 40° C. may be used. The progress of the cross-linking reaction is monitored using size-exclusion chromatography (SEC) of aliquots that are removed periodically from the reaction vessel. If the analysis is performed using a Pharmacia Superose-12 column, equilibrated and eluted with 1 M $MgCl_2$ in 50 mM bis tris buffer, pH 7, uncross-linked Hb dissociates into alpha, beta-dimers and elutes as a peak response with an apparent molecular weight of about 32 kiloDaltons (kDa). Intra-molecularly cross-linked Hb elutes more rapidly as a peak response with an apparent molecular weight of 64 kDa. Reaction is continued until the percentage of intra-molecularly cross-linked Hb in the reaction mixture exceeds 85%, as shown by the SEC profile.

The intra-molecular cross-linking reagents may be prepared separately using commercial reagents and conventional chemical reactions. For example, the oxirane 3,5-dibromosalicyl 3,4-oxabutanoate is a useful intra-molecular cross-linking reagent in the present invention and may be prepared in two steps as follows. 3,5-Dibromosalicyl 3-butenoate may be prepared by reaction of an acetone solution of 3-butenoyl chloride and 3,5-dibromosalicylic acid in the presence of 2,6-lutidine. The 3-butenoate ester is isolated and purified. In a second step, the desired oxirane, 3,5-dibromosalicyl 3,4-oxabutanoate, is prepared by reaction of 3,5-dibromosalicyl 3-butenoate and 3-chloroperbenzoic acid in chloroform solution.

In accordance with the present invention, each of at least five thiyl or amino groups on the surface of the Hb is joined covalently to a hydrodynamic volume-enhancing, anionic ligand having the formula:

wherein m is an integer from 1 to 100; and Z is $CH_2$—Hb, $CH(OH)CH_2$—Hb, $CH(SH)CH_2$—Hb, The ratio of moles of the compound to moles of Hb is about 5 to about 20. Preferably a ratio of about 10 moles of the compound to moles of Hb is employed. The reaction is performed at pH values of 6.5–8.5, and preferably at neutral pH. A reaction temperature of about 25° C. is preferred, but a reaction temperature in the range from about 4° C. to about 40° C. may be used. The progress of the reaction is monitored using size-exclusion chromatography (SEC) of aliquots that are removed periodically from the reaction vessel.

In a preferred embodiment of the present invention, a purified native mammalian or recombinant Hb is intra-molecularly cross-linked in accordance with the present invention and then further modified by joining covalently each of at least five amino or thiyl groups on the surface of the intra-molecularly cross-linked protein to the hydrodynamic volume-enhancing, anionic ligand. In a more preferred embodiment of the present invention, a purified porcine Hb is intra-molecularly cross-linked in accordance with the present invention and then further modified by joining covalently each of at least five amino or thiyl groups on the surface of the intra-molecularly cross-linked protein to the hydrodynamic volume-enhancing, anionic ligand. In another more preferred embodiment of the present invention, a purified recombinant Hb is intra-molecularly cross-linked in accordance with the present invention and then further modified by joining covalently each of at least five amino or thiyl groups on the surface of the intra-molecularly cross-linked protein to the hydrodynamic volume-enhancing, anionic ligand.

The decorating reagents useful for covalently joining a hydrodynamic volume-enhancing, anionic ligand of the present invention to a thiyl or amino group on the surface of a Hb may be prepared from commercial reagents using conventional chemical reactions. For example, α-carboxy, ω-maleimido-PEG, a useful decorating reagent, may be prepared by allowing a α-carboxy, ω-amino polyoxyethylene reagent (i.e., $^-OOC$-PEG-NH2) having a molecular weight of about 500 Daltons to react with N-oxysuccinimidyl 3-maleimidopropionate.

The present invention provides a method for delivering oxygen to cells or tissues comprising exposing said cells or tissues to a covalently modified hemoglobin composition of the present invention. In a preferred embodiment of the present invention, the temperatures of said exposing are equal to or less than 30° C.

Direct demonstrations of the oxygen delivering capability of a Hb composition may be difficult. Alternatively, the oxygen binding function and the $P_{50}$ value of the Hb may be used as surrogate measures of the capability for delivering oxygen at the partial pressure of oxygen in a cell or tissue. By these measures, effective oxygen delivery to working muscle (which has a partial pressure of oxygen of about 40 mmHg) and ischemic tissue (having a partial pressure of oxygen about 20 mmHg) is expected if the $P_{50}$ value of a Hb is approximately equal to or exceeds these values. Conversely, poor oxygen delivering capabilities are predicted for a Hb having a $P_{50}$ value significantly less than these values.

For example, the $P_{50}$ value of Hb in the human erythrocyte is about 28 mmHg at pH 7.4 and 37° C., but decreases to about 10 mmHg at 20° C. These data indicate that exposing cells or tissues to blood at 37° C. will effectively deliver oxygen to said cells or tissues, whereas exposing said cells or tissues to blood at 20° C. will not be useful for delivering oxygen to the cells or tissues. As a result, the cells or tissues may become or remain oxygen-poor or ischemic. In contrast, a covalently modified hemoglobin composition of the present invention having a biocompatible pH and an oxygen binding function, wherein said oxygen binding function has a temperature dependence of less than 0.023 units per degree Celsius, has a $P_{50}$ value at 20° C. that indicates said Hb delivers oxygen to cells or tissues at this low temperature. Moreover, a covalently modified hemoglobin composition of the present invention having a biocompatible pH and an oxygen binding function, wherein said oxygen binding function has a temperature dependence of less than 0.023 units per degree Celsius, has a $P_{50}$ value at 20° C. that indicates said Hb delivers oxygen to oxygen-poor or ischemic cells or tissues at this temperature.

Therefore, in another more preferred embodiment of the present invention, cells or tissues are exposed to a covalently modified porcine or recombinant hemoglobin composition having a biocompatible pH and an oxygen binding function, said oxygen binding function having a temperature dependence less than 0.023 units per degree Celsius. In a most preferred embodiment of the present invention, the cells or tissues are exposed to a covalently modified porcine hemoglobin composition having a biocompatible pH and an oxygen binding function, said oxygen binding function having a temperature dependence equal to or less than 0.016 units per degree Celsius. In another most preferred embodiment of the present invention, the cells or tissues are exposed to a covalently modified recombinant hemoglobin composition having a biocompatible pH and an oxygen binding function, said oxygen binding function having a temperature dependence equal to or less than 0.016 units per degree Celsius.

The present invention also provides a pharmaceutical composition comprising any of the hemoglobin compositions of the present invention and a pharmaceutically acceptable carrier. Suitable carriers include but are not limited to various physiologically acceptable solutions known in the art as normal saline solution, lactated Ringer's solution, or PlasmaLyte A solution. The pharmaceutical compositions also may comprise admixtures with blood, known plasma substitutes, and plasma expanders. Moreover, the pharmaceutical compositions may comprise encapsulated embodiments of any of the hemoglobin compositions of the present invention, such as liposome- or red cell ghost encapsulated compositions.

A covalently modified hemoglobin composition of the present invention may be administered by conventional means including but not limited to transfusion and injection.

A covalently modified hemoglobin composition of the present invention is useful for the replacement of blood volume lost through hemorrhage or surgery. Likewise, the Hb composition of the present invention is useful for the delivery of oxygen to cells and tissues in vivo or ex vivo. In a preferred embodiment, the Hb composition of the present invention is useful for the delivery of oxygen to cells and tissues at temperatures of 20° C. to 40° C. Moreover, the Hb composition of the present invention is useful for binding ligands such as nitric oxide or carbon monoxide, for example, when said ligands are present in concentrations or locations that may be deleterious to human health or the health of a tissue or organ intended for transplantation.

All publications cited herein are hereby incorporated by reference.

The present invention is described in the following Examples which are set forth to aid in the understanding of the invention, and should not be construed to limit in any way the invention as defined in the claims which follow thereafter.

EXAMPLES

Example 1

Preparation of purified porcine hemoglobin. An aqueous solution of purified porcine hemoglobin is prepared as described by Condo et al. (S. G. Condo et al. Molecular basis of low-temperature sensitivity in pig hemoglobins. Eur. J. Biochem. 209: 773–776, 1992). The hemoglobin concentration is adjusted to a value between 1 and 10 g/dL. If required, the aqueous, purified porcine deoxyHb is pasteurized at 60° C. for 10 hr.

Example 2

Preparation of 3,5-dibromosalicyl 3,4-oxabutanoate. 3,5-Dibromosalicyl 3-butenoate is prepared by reaction of an acetone solution of 3-butenoyl chloride and 3,5-dibromosalicylic acid in the presence of 2,6-lutidine. The 3-butenoate ester is isolated and purified. In a second step, the desired oxirane, 3,5-dibromosalicyl 3,4-oxabutanoate, is prepared by reaction of 3,5-dibromosalicyl 3-butenoate and 3-chloroperbenzoic acid in chloroform solution. The desired oxirane is isolated and purified.

Example 3

Preparation of α-carboxy, ω-maleimido-PEG. Alpha-carboxy,ω-amino polyoxyethylene (i.e., ⁻OOC—PEG—NH2) having a molecular weight of about 500 Daltons is allowed to react with N-oxysuccinimidyl 3-maleimidopropionate in small molar excess. The desired maleimide, α-carboxy, ω-maleimido-PEG is isolated and purified.

Example 4

Preparation of the covalently modified porcine hemoglobin CMPP-Hb. The processing equipment is suitably cleaned and sanitized or sterilized. A 3 g/dL solution of purified porcine Hb in water containing 10 moles of sodium tripolyphosphate is deoxygenated by repetitive passage through a membrane oxygenator charged with nitrogen gas. A nitrogen atmosphere is maintained in the reaction vessel throughout the ensuing operations. When the oxygen concentration is 200 ppm or less, a degassed solution of 2 mole equivalents of 3,5-dibromosalicyl 3,4-oxabutanoate is added, and the contents of the reaction vessel are maintained at temperatures of 20–30° C. After the addition is completed, the pH of the Hb solution is in the range 7–8. The cross-linking reaction is monitored by SEC analysis of aliquots removed periodically from the reaction vessel. When intramolecular cross-linking is complete, a degassed solution of 7 mole equivalents of α-carboxy,ω-maleimido-PEG is added. The decoration reaction is monitored by SEC analysis of aliquots removed periodically from the reaction vessel. When reaction is complete, the covalently modified porcine hemoglobin (which is identified by the acronym CMPP-Hb) is diafiltered against at least six volumes of PlasmaLyte A solution. The CMPP-Hb concentration is adjusted to about 7.5 g/dL, and the pH is adjusted to 7.3–7.5. One liter portions of CMPP-Hb are transferred aseptically to poly(ethylene-vinyl acetate) containers, which are sealed and labeled. If an inert atmosphere is maintained throughout the processing and packaging steps, as well as during the protein modification steps, the containers of deoxyCMPP-Hb are stored refrigerated. If the CMPP-Hb is allowed to re-oxygenate during the processing and packaging steps, the containers of oxyCMPP-Hb are stored at −5° C. or at lower temperatures. The oxygen binding function of CMPP-Hb is determined experimentally.

Example 5

Low-temperature survival of domestic swine after exchange transfusion with CMPP-Hb. Four domestic swine are anesthetized to permit surgical implantation of catheters for monitoring and for exchange transfusion of CMPP-Hb. The animals are allowed to recover. Baseline hemodynamic data are obtained, and blood samples are removed for determination of baseline values. Then each animal is immobilized, and one unit of blood is withdrawn through the arterial line and placed in a blood storage bag containing citrate-phosphate-dextrose-adenine blood storage solution. The shed blood is replaced with an equal volume of CMPP-Hb. After a brief equilibration period, this process is repeated until a porcine hematocrit of about 10% is achieved. The blood units are stored at 4° C. The animals are sedated, and cooling blankets and ice packs are used to lower body temperature to about 20° C. The animal is maintained at this temperature for 24 hr. Each animal is monitored continuously for signs of distress. Then warming blankets are used to raise body temperature to about 37° C., and the systemically circulating CMPP-Hb is exchanged with the pre-warmed, donated blood from that animal. The animals are allowed to recover. Forty-eight hours after the final exchange the animals are sacrificed, and organs and tissues are collected. No test-article related deaths are observed. Histopathological examination of the organs and tissues collected provides no evidence of adverse responses to the test article.

What is claimed is:

1. A covalently modified hemoglobin composition having a bioompatible pH and an oxygen binding function, wherein said oxygen binding function has a temperature dependence of less than about 0.023 units per degree Celsius; and wherein said covalently modified hemoglobin composition comprises a hemoglobin intra-molecularly cross-linked by reacting said hemoglobin with a reagent having the formula:

X—(CH$_2$)$_n$CO—Y wherein X is selected from the about consisting of halogen, sulfonate, phosphate, phosphonate, azide, oxirane, thiirane, azirane, malelmide and formyl: n is an integer from 0 to 8; and Y is a substituted activating ester or substituted activating thioester, wherein the activating esters are substituted with at least one anionic group selected from the group consisting of carboxyl, sulfate, sulfide, phosphonate, and phosphate; and having each of at least five thiyl or amino groups on the surface of said hemoglobin covalently joined to a hydrodynamic volume-enhancing, anionic ligand, wherein said ligand has the formula:

wherein m is an integer from 1 to 100; and Z is $CH_2$—Hb, $CH(OH)C_2$—Hb, $CH(SH)CH_2$—Hb,

, or

2. A covalently modified hemoglobin composition having a biocompatible pH and an oxygen binding function, wherein said oxygen binding function has a d(log $P_{50}$)/dT of less than about 0.023 units per degree Celsius; and wherein said covalently modified hemoglobin composition comprises a hemoglobin intra-molecularly cross-linked by reacting said hemoglobin with a reagent having the formula:

X—$(CH_2)_n$CO—Y wherein X is selected from the group consisting of halogen, sulfonate, phosphate, phosphonate, azide, oxirane, thiirane, azirane, maleimide and formyl; n is an integer from 0 to 8: and Y is a substituted activating ester or substituted activating thioester, wherein the activating esters are substituted with at least one anionic group selected from the group consisting of carboxyl, sulfate, sulfite, phosphonate, and phosphate: and having each of at least five thiyl or amino groups on the surface of said hemoglobin covalently joined to a hydrodynamic volume-enhancing, anionic ligand, wherein said ligand has the formula:

wherein m is an integer from 1 to 100: and Z is $CH_2$—Hb, $CH(OH)CH_2$—Hb, $CH(SH)CH_2$—Hb.

, or

3. The hemoglobin composition of claims 1 or 2, wherein said hemoglobin composition is a covalently modified porcine hemoglobin composition.

4. The hemoglobin composition of claims 1 or 2, wherein said hemoglobin composition is a covalently modified recombinant hemoglobin composition.

5. The hemoglobin composition of claim 1, wherein the temperature dependence of said oxygen binding function is equal to or less than 0.020 units per degree Celsius.

6. The hemoglobin composition of claim 1, wherein the temperature dependence of said oxygen binding function is equal to or less than 0.016 units per degree Celsius.

7. A covalently modified porcine hemoglobin composition having a pH of 6.5–8.5 and an oxygen binding function, wherein the temperature dependence of said oxygen binding function is equal to or less than 0.016 units per degree Celsius; and wherein said covalently modified porcine hemoglobin composition comprises a porcine hemoglobin intra-molecularly cross-linked by reacting said porcine hemoglobin with a reagent having the formula:

X—$(CH_2)_n$CO—Y wherein X is selected from the croup consisting of halogen, sulfonate, phosphate, phosphonate, azide, oxirane, thiirane, azirane, maleimide and formyl; n is an integer from 0 to 8: and Y is a substituted activating ester or substituted activating thioester, wherein the activating esters are substituted with at least one anionic group selected from the group consisting of carboxyl, sulfate, sulfite, phosphonate, and phosphate: and having each of at least five thiyl or amino groups on the surface of said hemoglobin covalently joined to a hydrodynamic volume-enhancing, anionic ligand, wherein said ligand has the formula:

wherein m is an integer from 1 to 100: and Z is $CH_2$—Hb, $CH(OH)CH_2$—Hb, $CH(SH)CH_2$—Hb, , or 8. A covalently modified recombinant hemoglobin composition having a pH of 6.5–8.5 and an oxygen binding function, wherein the temperature dependence of said oxygen binding function is equal to or less than 0.016 units per degree Celsius; and wherein said covalently modified recombinant hemoglobin composition comprises a recombinant hemoglobin intra-molecularly cross-linked by reacting said recombinant hemoglobin with a reagent having the formula:

wherein X is selected from the croup consisting of halogen, sulfonate, phosphate, phosphonate, azide, oxirane, thiirane, azirane, maleimide and formyl; n is an integer from 0 to 8: and Y is a substituted activating ester or substituted activating thioester, wherein the activating esters are substituted with at least one anionic group selected from the group consisting of carboxyl, sulfate, sulfite, phosphonate, and phosphate; and having each of at least five thyl or amino groups on the surface of said hemoglobin covalently joined to a hydrodynamic volume-enhancing, anionic ligand, wherein said ligand has the formula:

wherein m is an integer from 1 to 100: and Z is $CH_2$—Hb, $CH(OH)CH_2$—Hb, $CH(SH)CH_2$—Hb.

9. A method of preparing a covalently modified hemoglobin composition comprising:
  (a) intra-molecularly cross-linking a hemoglobin by reacting with a reagent having the formula:

$X$—$(CH_2)_n CO$—$Y$ wherein X is selected from the group consisting of halogen, sulfonate, phosphate, phosphonate, azide, oxirane, thiirane, azirane, maleimide and formyl; n is an integer from 0 to 8; and Y is a substituted activating ester or substituted activating thioester, wherein the activating esters are substituted with at least one anionic group selected from the group consisting of carboxyl, sulfate, sulfite, phosphonate, and phosphate; and
  (b) covalently joining each of at least five thiyl or amino groups on the surface of said hemoglobin to a hydrodynamic volume-enhancing, anionic ligand, wherein said ligand has the formula:

wherein m is an integer from 1 to 100; and Z is $CH_2$—Hb, $CH(OH)CH_2$—Hb, $CH(SH)CH_2$—Hb, 10. The method of claim 9, further comprising:
  (a) intra-molecularly cross-linking a porcine hemoglobin by reacting with a reagent having the formula:

$X$—$(CH_2)_n CO$—$Y$ wherein X is selected from the group consisting of halogen, sulfonate, phosphate, phosphonate, azide, oxirane, thiirane, azirane, maleimide and formyl; n is an integer from 0 to 8;

and Y is a substituted activating ester or substituted activating thioester, wherein the activating esters are substituted with at least one anionic group selected from the group consisting of carboxyl, sulfate, sulfite, phosphonate, and phosphate; and
  (b) covalently joining each of at least five thiyl or amino groups on the surface of said hemoglobin to a hydrodynamic volume-enhancing, anionic ligand, wherein said ligand has the formula:

wherein m is an integer from 1 to 100; and Z is $CH_2$—Hb, $CH(OH)CH_2$—Hb, $CH(SH)CH_2$—Hb,

11. The method of claim 9, further comprising:
  (a) intra-molecularly cross-linking a recombinant hemoglobin by reacting with a reagent having the formula:

$X$—$(CH_2)_n CO$—$Y$ wherein X is selected from the group consisting of halogen, sulfonate, phosphate, phosphonate, azide, oxirane, thiirane, azirane, maleimide and formyl; n is an integer from 0 to 8; and Y is a substituted activating ester or substituted activating thioester, wherein the activating esters are substituted with at least one anionic group selected from the group consisting of carboxyl, sulfate, sulfite, phosphonate, and phosphate; and
  (b) covalently joining each of at least five thiyl or amino groups on the surface of said hemoglobin to a hydrodynamic volume-enhancing, anionic ligand, wherein said ligand has the formula:

wherein m is an integer from 1 to 100; and Z is $CH_2$—Hb, $CH(OH)CH_2$ —Hb, $CH(SH)CH_2$—Hb, 12. A method of preparing a covalently modified porcine hemoglobin composition having a biocompatible pH and an oxygen binding function, wherein said oxygen binding function has a temperature dependence of less than or equal to 0.016 units per degree Celsius, comprising:

(a) intra-molecularly cross-linking a porcine hemoglobin by reacting with a reagent having the formula:

wherein X is selected from the group consisting of halogen, sulfonate, phosphate, phosphonate, azide, oxirane, thiirane, azirane, maleimide and formyl; n is an integer from 0 to 8; and Y is a substituted activating ester or substituted activating thioester, wherein the activating esters are substituted with at least one anionic group selected from the group consisting of carboxyl, sulfate, sulfite, phosphonate, and phosphate; and (b) covalently joining each of at least five thiyl or amino groups on the surface of said hemoglobin to a hydrodynamic volume-enhancing, anionic ligand, wherein said ligand has the formula:

wherein m is an integer from 1 to 100; and Z is $CH_2$—Hb, $CH(OH)CH_2$—Hb, $CH(SH)CH_2$—Hb,

13. A method of preparing a covalently modified recombinant hemoglobin composition having a biocompatible pH and an oxygen binding function, wherein said oxygen binding function has a temperature dependence of less than or equal to 0.016 units per degree Celsius, comprising:

(a) intra-molecularly cross-linking a recombinant hemoglobin by reacting with a reagent having the formula:

wherein X is selected from the group consisting of halogen, sulfonate, phosphate, phosphonate, azide, oxirane, thiirane, azirane, maleimide and formyl; n is an integer from 0 to 8; and Y is a substituted activating ester or substituted activating thioester, wherein the activating esters are substituted with at least one anionic group selected from the group consisting of carboxyl, sulfate, sulfite, phosphonate, and phosphate; and (b) covalently joining each of at least five thiyl or amino groups on the surface of said hemoglobin to a hydrodynamic volume-enhancing, anionic ligand, wherein said ligand has the formula:

wherein m is an integer from 1 to 100; and Z is $CH_2$—Hb, $CH(OH)CH_2$—Hb, $CH(SH)CH_2$—Hb,

14. A method of delivering oxygen to cells or tissues comprising exposing said cells or tissues to the covalently modified hemoglobin composition of claims 1 or 2.

15. The method of delivering oxygen of claim 14 wherein the temperature of said exposing is equal to or less than 30° C.

16. A method of delivering oxygen to cells or tissues comprising exposing said cells or tissues to a covalently modified porcine hemoglobin composition having a biocompatible pH and an oxygen binding function, wherein said oxygen binding function has a temperature dependence of equal to or less than 0.016 units per degree Celsius, wherein the temperature of said exposing is equal to or less than 30° C.; and wherein said covalently modified porcine hemoglobin composition comprises a porcine hemoglobin intra-molecularly cross-linked by reacting said porcine hemoglobin with a reagent having the formula:

wherein X is selected from the group consisting of halogen, sulfonate, phosphate, phosphonate, azide, oxirane, thiirane, azirane, maleimide and formyl; n is an integer from 0 to 8; and Y is a substituted activating ester or substituted activating thioester, wherein the activating esters are substituted with at least one anionic group selected from the group consisting of carboxyl, sulfate, sulfite, phosphonate, and phosphate; and having each of at least five thiyl or amino groups on the surface of said porcine hemoglobin covalently joined to a hydrodynamic volume-enhancing, anionic ligand, wherein said ligand has the formula:

wherein m is an integer from 1 to 100: and Z is $CH_2$—Hb, $CH(OH)CH_2$—Hb, $CH(SH)CH_2$—Hb.

17. A method of delivering oxygen to cells or tissues comprising exposing said cells or tissues to a covalently modified recombinant hemoglobin composition having a biocompatible pH and an oxygen binding function, wherein said oxygen binding function has a temperature dependence of equal to or less than 0.016 units per degree Celsius, wherein the temperature of said exposing is equal to or less than 30° C.; and wherein said covalently modified recombinant hemoglobin composition comprises a recombinant hemoglobin intra-molecularly cross-linked by reacting said recombinant hemoglobin with a reagent having the formula:

wherein X is selected from the croup consisting of halogen, sulfonate, phosphate, phosphonate, azide, oxirane, thiirane, azirane, mnaleimide and formyl; n is an integer from 0 to 8: and Y is a substituted activating ester or substituted activating thioester, wherein the activating esters are substituted with at least one anionic group selected from the group consisting of carboxyl. sulfate, sulfite, phosphonate, and phosphate; and having each of at least five thiyl or amino groups on the surface of said recombinant hemoglobin covalently joined to a hydrodynamic volume-enhancing, anionic ligand, wherein said ligand has the formula:

wherein m is an integer from 1 to 100: and Z is CH$_2$—Hb, CH(OH)CH$_2$—Hb, CH(SH)CH$_2$—Hb, 18. A covalently modified hemoglobin composition comprising:

a hemoglobin intra-molecularly cross-linked by reacting said hemoglobin with a reagent having the formula:

wherein X is selected from the group consisting of halogen, sulfonate, phosphate, phosphonate, azide, oxirane, thiirane, azirane, maleimide and formyl; n is an integer from 0 to 8; and Y is a substituted activating ester or substituted activating thioester, wherein the activating esters are substituted with at least one anionic group selected from the group consisting of carboxyl, sulfate, sulfite, phosphonate, and phosphate; and having each of at least five thiyl or amino groups on the surface of said hemoglobin covalently joined to a hydrodynamic volume-enhancing, anionic ligand, wherein said ligand has the formula:

wherein m is an integer from 1 to 100; and Z is CH$_2$—Hb, CH(OH)CH$_2$—Hb, CH(SH)CH$_2$—Hb, 19. The covalently modified hemoglobin composition of claim 18, further comprising:

a porcine hemoglobin intra-molecularly cross-linked by reacting said porcine hemoglobin with a reagent having the formula:

wherein X is selected from the group consisting of halogen, sulfonate, phosphate, phosphonate, azide, oxirane, thuilane, azirane, maleimide and formyl; n is an integer from 0 to 8; and Y is a substituted activating ester or substituted activating thioester, wherein the activating esters are substituted with at least one anionic group selected from the group consisting of carboxyl, sulfate, sulfite, phosphonate, and phosphate; and having each of at least five thiyl or amino groups on the surface of said porcine hemoglobin covalently joined to a hydrodynamic volume-enhancing, anionic ligand, wherein said ligand has the formula:

wherein m is an integer from 1 to 100; and Z is CH$_2$—Hb, CH(OH)CH$_2$—Hb, CH(SH)CH$_2$—Hb, 20. The covalently modified hemoglobin composition of claim 18, further comprising:

a recombinant hemoglobin intra-molecularly crosslinked by reacting said recombinant hemoglobin with a reagent having the formula:

wherein X is selected from the group consisting of halogen, sulfonate, phosphate, phosphonate, azide, oxirane, thiirane, azirane, maleimide and formyl; n is an integer from 0 to 8; and Y is a substituted activating ester or substituted activating thioester, wherein the activating esters are substituted with at least one anionic group selected from the group consisting of carboxyl, sulfate, sulfite, phosphonate, and phosphate; and having each of at least five thiyl or amino groups on the surface of said recombinant hemoglobin covalently joined to a hydrodynamic volume-enhancing, anionic ligand, wherein said ligand has the formula:

wherein m is an integer from 1 to 100; and Z is CH$_2$—Hb, CH(OH)CH$_2$—Hb, CH(SH)CH$_2$—Hb, , or 21. A covalently modified porcine hemoglobin composition having a biocompatible pH and an oxygen binding function, comprising:

a porcine hemoglobin intra-molecularly cross-linked by reacting said porcine hemoglobin with a reagent having the formula:

X—(CH$_2$)$_n$CO—Y wherein X is selected from the group consisting of halogen, sulfonate, phosphate, phosphonate, azide, oxirane, thiirane, azirane, maleimide and formyl; n is an integer from 0 to 8; and Y is a substituted activating ester or substituted activating thioester, wherein the activating esters are substituted with at least one anionic group selected from the group consisting of carboxyl, sulfate, sulfite, phosphonate, and phosphate; and having each of at least five thiyl or amino groups on the surface of said porcine hemoglobin covalently joined to a hydrodynamic volume-enhancing, anionic ligand, wherein said ligand has the formula:

wherein m is an integer from 1 to 100; and Z is CH$_2$—Hb, CH(OH)CH$_2$—Hb, CH(SH)CH$_2$—Hb, , or and wherein said oxygen binding function has a temperature dependence of less than or equal to 0.016 units per degree Celsius.

22. A covalently modified recombinant hemoglobin composition having a biocompatible pH and an oxygen binding function, comprising:

a recombinant hemoglobin intramolecularly cross-linked by reacting said recombinant hemoglobin with a reagent having the formula:

X—(CH$_2$)$_n$CO—Y wherein X is selected from the group consisting of halogen, sulfonate, phosphate, phosphonate, azide, oxirane, thiurane, azirane, maleimide and formyl; n is an integer from 0 to 8; and Y is a substituted activating ester or substituted activating thioester, wherein the activating esters are substituted with at least one anionic group selected from the group consisting of carboxyl, sulfate, sulfite, phosphonate, and phosphate; and having each of at least five thiyl or amino groups on the surface of said recombinant hemoglobin covalently joined to a hydrodynamic volume-enhancing, anionic ligand, wherein said ligand has the formula:

wherein m is an integer from 1 to 100; and Z is CH$_2$—Hb, CH(OH)CH$_2$—Hb, CH(SH)CH$_2$—Hb, , or and wherein said oxygen binding function has a temperature dependence of less than or equal to 0.016 units per degree Celsius.

* * * * *